United States Patent
Yin et al.

(10) Patent No.: US 6,726,901 B2
(45) Date of Patent: Apr. 27, 2004

(54) STABILIZED ANTIPERSPIRANT COMPOSITIONS CONTAINING ALUMINUM-ZIRCONIUM SALTS WITH LOW M:CL RATIO

(75) Inventors: Yuling Yin, Quincy, MA (US); Jayant N. Sane, Framingham, MA (US); Yan-Fei Shen, Canton, MA (US)

(73) Assignee: The Gillette Company, Boston, MA (US)

( * ) Notice: Subject to any disclaimer, the term of this patent is extended or adjusted under 35 U.S.C. 154(b) by 42 days.

(21) Appl. No.: 10/142,140

(22) Filed: May 9, 2002

(65) Prior Publication Data

US 2003/0211060 A1 Nov. 13, 2003

(51) Int. Cl.⁷ .................. A61K 7/32; A61K 7/34; A61K 7/38; A61K 7/00
(52) U.S. Cl. .................. 424/65; 424/66; 424/68; 424/400; 424/401
(58) Field of Search .................. 424/65, 66, 68, 424/400, 401

(56) References Cited

U.S. PATENT DOCUMENTS

| | | | |
|---|---|---|---|
| 2,814,585 A | 11/1957 | Daley | 167/90 |
| 2,854,382 A | 9/1958 | Grad | 167/90 |
| 3,981,986 A | 9/1976 | Rubino | 424/47 |
| 4,017,599 A | 4/1977 | Rubino | 424/47 |
| 4,331,609 A | 5/1982 | Orr | 260/468 |
| 4,774,079 A * | 9/1988 | Shin et al. | 424/66 |
| 4,775,528 A | 10/1988 | Callaghan | 424/66 |
| 4,871,525 A | 10/1989 | Giovanniello et al. | 423/463 |
| 4,900,534 A | 2/1990 | Inward | 423/463 |
| 5,225,187 A | 7/1993 | Carmody | 424/66 |
| 5,296,623 A | 3/1994 | Katsoulis et al. | 424/66 |
| 5,330,751 A | 7/1994 | Curtin | 424/66 |
| 5,354,553 A | 10/1994 | Greczyn et al. | 424/65 |
| 5,443,822 A | 8/1995 | Greczyn et al. | 424/65 |
| 5,718,876 A | 2/1998 | Parekh | 424/65 |
| 5,955,064 A | 9/1999 | Giovanniello | 424/65 |
| 5,955,065 A | 9/1999 | Thong | 424/68 |
| 6,024,945 A | 2/2000 | Parekh | 424/68 |
| 6,066,314 A | 5/2000 | Tang | 424/65 |
| 6,126,928 A | 10/2000 | Swaile | 424/65 |
| 6,375,937 B1 | 4/2002 | Chopra | 424/65 |
| 6,517,819 B1 | 2/2003 | Breker et al. | 424/65 |
| 2003/0049219 A1 | 3/2003 | Lemoine et al. | 424/66 |

FOREIGN PATENT DOCUMENTS

| | | |
|---|---|---|
| CA | 1153313 | 9/1983 |
| EP | 653203 | 5/1995 |
| EP | 1284128 | 2/2003 |
| GB | 1353916 | 5/1974 |
| WO | 01/56539 | 8/2001 |
| WO | 02/34223 | 5/2002 |

* cited by examiner

Primary Examiner—Shelley A. Dodson
(74) Attorney, Agent, or Firm—Stephan P. Williams

(57) ABSTRACT

Disclosed is an anhydrous topical antiperspirant composition comprising a dermatologically acceptable carrier and a perspiration reducing effective amount of a particulate antiperspirant salt suspended in the carrier. The antiperspirant salt comprises an aluminum-zirconium chlorohydrate having a metal to chloride ratio between about 0.9 and about 1.3. The composition also includes, separate from the antiperspirant salt, a stabilizing basic material in an amount sufficient to prevent degradation of the antiperspirant composition or to minimize acid odor. Also disclosed is a method of reducing perspiration from human skin by applying the aforementioned topical composition.

19 Claims, No Drawings

STABILIZED ANTIPERSPIRANT COMPOSITIONS CONTAINING ALUMINUM-ZIRCONIUM SALTS WITH LOW M:CL RATIO

BACKGROUND OF THE INVENTION

The present invention relates to antiperspirant compositions comprising an aluminum-zirconium antiperspirant salt with a low metal to chloride ratio (e.g., M:Cl=0.9–1.3) and a stabilizing basic material.

Aluminum-zirconium antiperspirant salts have been known for several decades. See, for example, U.S. Pat. No. 2,814,585 (Daley), U.S. Pat. No. 2,854,382 (Grad), GB 1,353,916 (Bolich), U.S. Pat. No. 4,331,609 (Orr), U.S. Pat. No. 4,775,528 (Callaghan), U.S. Pat. No. 4,871,525 (Giovanniello), U.S. Pat. No. 4,900,534 (Inward), U.S. Pat. No. 5,225,187 (Carmody), U.S. Pat. No. 5,296,623 (Katsoulis), U.S. Pat. No. 5,330,751 (Curtin), EP 653,203 (Rosenberg), U.S. Pat. No. 5,718,876 (Parekh) and U.S. Pat. No. 5,955,064 (Giovanniello). Some of these aluminum-zirconium antiperspirant salts are described as having enhanced efficacy, which means that they provide greater sweat reduction than conventional antiperspirant salts.

The enhanced efficacy salts are typically differentiated from conventional antiperspirant salts by reference to the various aluminum peaks that can be identified when the salt is analyzed by size exclusion chromatography, typically HPLC (high pressure liquid chromatography). A suitable chromatographic technique must be capable of resolving the Al into at least four distinct peaks (labeled peaks 2 (or 1+2), 3, 4 and 5), such as is shown in U.S. Pat. No. 5,330,751. Up to now, the enhanced efficacy salts have been described as having an increased peak 4 content or an increased peak 4 to peak 3 ratio compared to conventional salts. (In some cases, enhanced salts have been described as having increased "band III" content by some authors, depending on the chromatographic technique and nomenclature employed. Generally, bands I, II, III and IV of one system correspond to peaks 1+2 (band I), 3, 4 and 5 of the other system.) Typically, the known enhanced efficacy salts (measured as 10% solutions) have an HPLC peak 4 to peak 3 area ratio of 0.5 or higher, preferably at least 0.7, with at least 70%, preferably at least 80%, of the aluminum contained in peaks 3 and 4. Thus, the enhanced salts will typically have a peak 4 content of at least 30% of the total aluminum contained in all the peaks (measured by peak area). In contrast, conventional non-enhanced antiperspirant salts have a negligible peak 4 content or a peak 4 to 3 area ratio less than 0.2, typically about 0.1.

Prior to the discovery of the enhanced Al—Zr salts as described above, U.S. Pat. No. 4,331,609 suggested that Al—Zr salts with a metal to chloride ratio below about 1.3 (e.g., 1.25) may be more efficacious than salts with a higher metal to chloride ratio. However, this efficacy claim does not appear to have gained acceptance in the industry. In U.S. Pat. No. 6,126,928 there are described certain polyhydric alcohol solutions of the salts described in the aforementioned '609 patent. More recently, U.S. Pat. No. 6,375,937 described aluminum-zirconium tetrachlorohydrex glycine salts having a metal to chloride ratio in the range of 0.9 to 1.2 and a glycine to zirconium ratio greater than 1.3.

In WO 02/34223 there is described a new type of enhanced efficacy aluminum-zirconium antiperspirant salt having a high peak 5 aluminum content. These salts, which are given the shorthand designation "$E^5$AZCH", generally exhibit an HPLC peak 5 area content greater than 33%, preferably greater than 45%. This disclosure suggests that preferred salts will have a metal (Al+Zr) to chloride ratio of about 0.90 to about 1.00.

In U.S. Pat. No. 6,024,945 there are described aerosol antiperspirant compositions which include certain additives to prevent the formation of toxic compounds that may result from the reaction of aluminum chlorohydrate and the propellant, 1,1-difluoroethane. The additives include, for example, an amino acid, an amino compound, a metal glycinate, a hydrotalcite, a complex aluminum buffering agent, etc.

Aluminum-zirconium antiperspirant salts which have a low metal to chloride (or halogen) ratio are very acidic. Such acidic salts are difficult to formulate into conventional anhydrous compositions because they can destabilize or degrade the composition or decompose one or more of its components. In the case of a solid product, the hardness of the product will deteriorate significantly over time. In the case of a cream or soft solid product, the viscosity of the product will deteriorate. In adddition, such products can have an undesirable acid odor. While it is possible to neutralize some of the salt acidity by adding some basic material to the aqueous salt (e.g., by addition of amino acid to increase the amino acid to zirconium ratio) during its manufacture, this type of neutralization is a chemical process that can alter the chemistry of the salts being neutralized. It has been found that such neutralization can adversely impact the antiperspirant efficacy of the salt so that it does not achieve its highest possible efficacy.

It would be highly desirable to provide a stabilized anhydrous salt with a low metal to chloride ratio. Such a composition should retain the inherent efficacy of the salt, while being stable against degradation under normal storage conditions. Also, it is highly desirable to eliminate the acid odor from products containing antiperspirant salts with a low metal to chloride ratio.

SUMMARY OF THE INVENTION

The present invention embraces an anhydrous topical antiperspirant composition comprising a dermatologically acceptable carrier and a perspiration reducing effective amount of a particulate antiperspirant salt suspended in the carrier. The antiperspirant salt comprises an aluminum-zirconium chlorohydrate having a metal to chloride ratio between about 0.9 and about 1.3. The composition also includes, separate from the antiperspirant salt, a stabilizing basic material (as hereinafter described) in an amount sufficient to prevent degradation of the antiperspirant composition or to minimize acid odor. The present invention also embraces a method of reducing perspiration from human skin by applying the aforementioned antiperspirant composition.

DETAILED DESCRIPTION OF THE INVENTION

The anhydrous topical antiperspirant composition of the present invention comprises a dermatologically acceptable carrier, a perspiration reducing effective amount of a particulate antiperspirant salt suspended in the carrier, and, as a separate material from said antiperspirant salt, a stabilizing basic material in an amount sufficient to prevent degradation of the antiperspirant composition. The term "anhydrous" as used herein means that the composition is substantially free (that is, contains less than about 2%, preferably less than 1%, and most preferably less than 0.1% by weight) of free water (excluding any water of hydration associated with the antiperspirant salt or other components of the composition).

The particulate antiperspirant salt comprises an aluminum-zirconium chlorohydrate having a metal to chloride ratio between about 0.9 and about 1.3, preferably between about 0.9 and 1.1, and most preferably between about 0.9 and 1.0. The aluminum-zirconium chlorohydrate will generally have the empirical formula $Al_nZr(OH)_{[3n+4-m(n+1)]}(Cl)_{[m(n+1)]}$ where n is 2.0 to 10.0, preferably 3.0 to 8.0, and m is about 0.77 to 1.11 (which corresponds to a metal (Al+Zr) to chloride ratio of about 1.3–0.9), preferably about 0.91 to about 1.11 (which corresponds to M:Cl= 1.1–0.9), and most preferably about 1.00 to about 1.11 (which corresponds to M:Cl=1.0–0.9). These salts also generally have some water of hydration associated with them, typically on the order of 1 to 5 moles per mole of salt (typically, about 1% to about 16%, more typically about 4% to about 13% by weight). Normally these salts will also include an amino acid associated with them to prevent polymerization of the zirconium species during manufacture. Typical amino acids include glycine, alanine, valine, serine, leucine, and aminobutyric acid, with glycine (or its salts) being preferred. If included, the amino acid is present in an amount of about 1 to 3 moles, preferably about 1.3 to 1.8 moles, of amino acid per mole of zirconium in the salt.

The preferred antiperspirant salts include aluminum-zirconium tetrachlorohydrate (Al:Zr=2–6; M:Cl=0.9–1.3) and aluminum-zirconium octachlorohydrate (Al:Zr=6–10; M:Cl=0.9–1.3), especially salts with a metal to chloride ratio of about 0.9 to 1.1, most preferably about 0.9 to 1.0. In addition, to achieve the greatest antiperspirant efficacy it is most advantageous to utilize an enhanced efficacy antiperspirant salt, particularly one having a high peak 5 aluminum content. The most preferred of these salts, when analyzed by HPLC as a 10% aqueous solution using conditions capable of resolving the aluminum into at least four successive peaks (labeled peaks 2 to 5), exhibits an HPLC peak 5 area of at least 33%, more preferably at least 45%, based on the total area of HPLC peaks 2 to 5. In addition to having a high peak 5 content, it is also preferred, for maximum efficacy, that the salt have an HPLC peak 4 to peak 3 area ratio of at least 0.4, preferably at least 0.7, and most preferably at least 0.9. The high peak 5 aluminum-zirconium salts (also designated "$E^5AZCH$") are more completely described in WO 02/34223, which is incorporated herein by reference.

The powdered antiperspirant salt is suspended in an anhydrous, dermatologically acceptable carrier, particularly a carrier comprising a silicone (e.g., cyclomethicone, dimethicone, etc.), typically at a concentration of about 6% to about 22% (USP) active by weight.

The antiperspirant composition of the present invention also includes, separate from the antiperspirant salt, a stabilizing basic material in an amount sufficient to prevent degradation of the antiperspirant composition or to minimize acid odor. The stabilizing basic material will typically be present in an amount of about 0.1% to 10%, preferably about 0.5% to 3%, by weight. Such basic material must be safe for use in personal care products (i.e., dermatologically acceptable).

The stabilizing basic material can be selected from materials falling within the following four categories:

1) The salts formed by a strong base (such as sodium hydroxide) and a weak acid (pKa>1, such as acetic acid). Examples include sodium carbonate, sodium bicarbonate, sodium acetate, potassium carbonate, potassium bicarbonate, sodium gluconate, sodium benzoate, sodium citrate, sodium phosphate, sodium hydrogenphosphate, sodium dihydrogenphosphate, sodium lactate, sodium tetraborate, (di-, tri- or tetra-) sodium EDTA, etc.
2) Amino acids that are basic (pH>7, preferably pH>8) in aqueous solution. Examples include glycine, lysine, tyrosine and arginine.
3) Salts formed by a strong base and an amino acid. Examples include sodium glycinate, sodium tyrosinate, calcium glycinate, sodium lysinate, magnesium glycinate and strontium glycinate
4) Inorganic bases that are not soluble in water. Examples include alkaline earth oxides such as magnesium oxide, calcium oxide, and strontium oxide, and other basic oxides such as zinc oxide, magnesium aluminate, sodium silicate, sodium magnesium silicate, etc.

Materials within the above four categories may be readily screened for suitability by incorporating a candidate material (at a level of 1–3% by weight) into a standard antiperspirant stick composition (such as shown in Example 1 set out hereinafter) and measuring any diminution in stick hardness (as described hereinafter) after aging the stick for one month at 45° C. Suitable stabilizing materials will be those which prevent diminution in stick hardness by 30% or less, preferably by 20% or less. The more preferred basic stabilizing materials include sodium glycinate, lysine, and sodium carbonate, with lysine and sodium glycinate being most preferred. Additional, but somewhat less preferred, suitable materials include glycine, tyrosine, arginine and sodium gluconate. Of course, mixtures of two or more of the above materials may be used in combination.

The antiperspirant composition further includes a dermatologically acceptable anhydrous carrier into which the antiperspirant salt and the basic material are suspended. While the carrier may include some lower alkanol (up to 15% or so), it is preferred that the carrier vehicle is substantially free (that is, contains less than 5%, preferably less than 2%, more preferably less than 1%, and most preferably less than 0.1%) of lower alkanol such as ethanol.

The anhydrous carrier may comprise any of the ingredients commonly utilized in the formulation of topical antiperspirant compositions. Advantageously, the carrier vehicle will comprise one or more volatile silicones, which evaporate quickly and provide a dry feel. The volatile silicones include the cyclic polydimethylsiloxanes, also known as cyclomethicones, which have from about three to about seven silicon atoms, and the linear polydimethylsiloxanes, also known as dimethicones, which have from about 2 to about 8 silicon atoms. The linear volatile silicones generally have viscosities of less than 5 cst, while the cyclic volatile silicones have viscosities under 10 cst. Mixtures of volatile silicones may be advantageously employed. When included in the carrier, the volatile silicones are typically present in an amount of about 10% to 90%, more typically about 20% to 70%, by weight.

The carrier may optionally include a liquid non-volatile emollient to improve emolliency and application aesthetics (e.g., reduced tackiness, slower dry-down, reduced drag and reduced whitening). The non-volatile emollient may be generally included in an amount of about 0% to about 25%, preferably about 2% to about 20%, more preferably about 5% to about 15%, by weight. Preferably the amount of non-volatile emollient will be less than about one-half the amount of volatile silicone present in the composition, and more preferably will be less than about one-third the amount of volatile silicone. Generally, the amount of non-volatile emollient should be kept to a minimum so as not to adversely affect efficacy.

When present, the non-volatile emollient will typically have a viscosity of about 5 to about 1000 cst, preferably about 10 to 500 cst. Examples of non-volatile emollients include the non-volatile silicones, typically polyalkylsiloxanes such as dimethicone (e.g. DC 200) and polyalkylarylsiloxanes such as phenyltrimethicone (e.g. DC 556), paraffinic hydrocarbons such as mineral oil and hydrogenated polyisobutene, aliphatic alcohols such as octyldodecanol, fatty alcohol esters such as $C_{12-15}$ alcohols benzoate and myristyl octanoate, fatty acid esters such as isopropyl palmitate, myristyl myristate and octyl isononanoate, dicarboxylic acid esters such as diisopropyl sebacate, polyethylene glycols and polypropylene glycols such as PEG-40 and PPG-20, polyethylene and/or polypropylene glycol ethers of $C_{4-20}$ alcohols such as PPG-10 butanediol, PPG-14 butyl ether, PPG-5-Buteth-7, PPG-3-Myreth-3, and Steareth-20, and polyethylene and/or polypropylene glycol esters of $C_{4-20}$ acids such as PEG-8 Distearate and PEG-10 Dioleate. Preferred emollients include the ethoxylated and propoxylated ethers and esters of $C_{4-20}$ alcohols and acids. Of course, more than one emollient may be used.

The carrier may include polyhydric alcohols such as propylene glycol, dipropylene glycol, glycerine, and 1,2-hexanediol. The carrier may also include waxes such as fatty alcohols, for example, stearyl alcohol, cetyl alcohol, and myristyl alcohol, fatty amides, for example, Stearamide MEA and Lauramide DEA, hydrogenated castor oil (castor wax), silicone wax and polyethylene homopolymer, gelling agents such as 12-hydroxystearic acid (including esters and amides thereof) and glyceryl tribehenate, N-acyl amino acid amides such as N-lauroyl-L-glutamic acid-di-n-butyl amide and alkyl amides such as 2-dodecyl-N,N'-dibutylsuccinamide, thickeners such as silicone latex or silicone elastomer, suspending agents such as clays (e.g. quaternium-18 hectorite) and silicas, and fillers such as talc, polyolefins and modified corn starch. Naturally, of course, the antiperspirant composition will also ideally include a fragrance.

The foregoing list of materials is by way of example only and is not intended to be a comprehensive list of all potential materials that may be useful in an antiperspirant composition. Obviously, the skilled worker may select materials which provide the desired application and aesthetic characteristics of the particular form of antiperspirant composition to be produced.

The topical antiperspirant composition of the present invention may be formulated as a lotion, cream, gel, soft-solid, solid stick, etc. A cream, soft-solid or solid stick is preferred, with a solid stick being more preferred. The solid stick will preferably have a hardness of about 100 to 600 grams, preferably about 150 to 500 grams, most preferably about 200 to 400 grams. Stick hardness is measured in grams using a TA-XT2 Texture Analyzer from Texture Technologies Corp. with a cone-shaped needle (TA-17, 30° cone), a cursor speed of 1.0 mm/sec and a penetration distance of 5 mm. Ideally, the stick hardness will be relatively stable—that is, preferably its hardness will degrade by not more than 30%, most preferably not more than 20%—when the product is aged for one month at 45° C.

The present invention also embraces a method of inhibiting or reducing perspiration by topically applying an effective amount of an anhydrous antiperspirant composition as described herein to the skin of a human, preferably to the axilla, where such reduction in perspiration is desired. An effective amount is that amount which provides at least a 20% sweat reduction, preferably at least a 40% sweat reduction, when tested in accordance with a standard hot room thermal efficacy protocol, and most preferably that amount which reduces perspiration to a degree that is noticeable by the user. Typically, the amount of antiperspirant composition applied will range from about 0.1 gram to about 1.0 gram per axilla depending on the formulation or such amount as will deliver about 0.01 to about 0.25 gram of antiperspirant active per axilla.

The present invention may be further illustrated by the following examples in which the parts and percentages are by weight. $E^5AZCH$, when used in the examples, means an enhanced efficacy aluminum-zirconium chlorohydrate having an HPLC peak 5 area greater than 40% and a metal (Al+Zr) to chloride ratio between 0.9 and 1.0. This salt was made in accordance with the procedure set out in WO 02/34223.

EXAMPLES 1 TO 3

Solid Stick Antiperspirant

Solid stick antiperspirant compositions are prepared having the ingredients and the amounts set out below. Each of these compositions is prepared by mixing all of the ingredients (except the fragrance) with the cyclomethicone, heating the mixture to melt the gelling agents, and cooling the mixture to form a solid stick, with the fragrance being added during the cooling step and prior to solidification. The example labeled "Comp." is a comparative example that does not include any stabilizing basic material.

|  | Weight Percent | | | |
|---|---|---|---|---|
| Ingredient | Comp. | Ex. 1 | Ex. 2 | Ex. 3 |
| Cyclomethicone (DC 245) | 41.39 | 40.57 | 40.57 | 40.57 |
| $E^5AZCH$ | 19.00 | 18.62* | 18.62* | 18.62* |
| Stearyl alcohol | 21.50 | 21.07 | 21.07 | 21.07 |
| PPG-14 butyl ether | 11.00 | 10.78 | 10.78 | 10.78 |
| Hydrogenated castor wax | 2.84 | 2.78 | 2.78 | 2.78 |
| Myristyl myristate | 1.92 | 1.88 | 1.88 | 1.88 |
| Silica (R972 & A300) | 1.80 | 1.76 | 1.76 | 1.76 |
| Fragrance | 0.55 | 0.54 | 0.54 | 0.54 |
| Sodium glycinate |  | 2.00 |  |  |
| Lysine |  |  | 2.00 |  |
| Sodium carbonate |  |  |  | 2.00 |

*Approximately 14.5% USP active

The above compositions are tested for stability by storing for one month at 45° C. Stick hardness is measured before and after the high temperature storage using the TA-XT2 Texture Analyzer previously described.

| Stick Hardness (grams) | | | | |
|---|---|---|---|---|
|  | Comp. | Ex. 1 | Ex. 2 | Ex. 3 |
| Before High Temp. Storage | 302 | 422 | 394 | 431 |
| After High Temp. Storage | 177 | 379 | 363 | 285 |

As can be seen from the above data, initial stick hardness for all the compositions is greater than 300 grams. After high temperature storage for one month, the stick without any stabilizing basic material (Comp.) has a dramatic drop in hardness to an unacceptable level (<200 grams). The sticks which include a basic stabilizing material (Ex. 1–3) maintain stick hardness at an acceptable level (>250 grams). In fact, the sticks containing sodium glycinate or lysine as the stabilizing material (Ex. 2 and Ex. 3), maintain hardness well above 300 grams. The sticks also do not have unacceptable acid odor.

EXAMPLES 4 TO 6

Solid Stick Antiperspirant

Solid stick antiperspirant compositions are prepared as above having the ingredients and the amounts set out below.

| | Weight Percent | | |
|---|---|---|---|
| Ingredient | Ex. 4 | Ex. 5 | Ex. 6 |
| Cyclomethicone (DC 245) | 40.98 | 40.98 | 40.98 |
| E⁵AZCH | 18.81* | 18.81* | 18.81* |
| Stearyl alcohol | 21.29 | 21.29 | 21.29 |
| PPG-14 butyl ether | 10.89 | 10.89 | 10.89 |
| Hydrogenated castor wax | 2.81 | 2.81 | 2.81 |
| Myristyl myristate | 1.90 | 1.90 | 1.90 |
| Silica (R972 & A300) | 1.78 | 1.78 | 1.78 |
| Fragrance | 0.54 | 0.54 | 0.54 |
| Sodium glycinate | 1.00 | | |
| Lysine | | 1.00 | |
| Sodium carbonate | | | 1.00 |

*Approximately 14.6% USP active

The above compositions are tested for stability by storing for one month at 45° C. Stick hardness is measured before and after the high temperature storage using the TA-XT2 Texture Analyzer previously described.

| | Stick Hardness (grams) | | |
|---|---|---|---|
| | Ex. 4 | Ex. 5 | Ex. 6 |
| Before High Temp. Storage | 312 | 320 | 300 |
| After High Temp. Storage | 260 | 255 | 253 |

As can be seen from the above data, even with a reduced level of basic stabilizing material, the sticks maintain hardness at an acceptable level (>250 grams).

EXAMPLES 7 TO 8

Cream Antiperspirant

Cream (or soft solid) antiperspirant compositions are prepared having the ingredients and the amounts set out below. Each of these compositions is prepared by mixing all of the ingredients (except the fragrance) to form a homogeneous suspension, heating to about 75–90° C. to melt and dissolve the polyethylene homopolymer, and cooling the mixture to form a stiff cream or soft solid, with the fragrance being added during the cooling step. These compositions maintain their viscosity during storage and do not have unacceptable acid odor.

| | Weight Percent | |
|---|---|---|
| Ingredient | Ex. 7 | Ex. 8 |
| Cyclomethicone (DC 245) | 55.5 | 55.5 |
| E⁵AZCH | 23.0* | 23.0* |
| Dimethicone (50 cst.) | 15.0 | 15.0 |
| Polyethylene (MW ≅ 400) | 4.0 | 4.0 |

-continued

| | Weight Percent | |
|---|---|---|
| Ingredient | Ex. 7 | Ex. 8 |
| Fragrance | 0.5 | 0.5 |
| Sodium glycinate | 2.0 | |
| Lysine | | 2.0 |

*Approximately 17.9% USP active

What is claimed is:

1. An anhydrous topical antiperspirant composition comprising a dermatologically acceptable carrier, a perspiration reducing effective amount of a particulate antiperspirant salt suspended in the carrier, wherein the antiperspirant salt comprises an aluminum-zirconium chlorohydrate having a metal to chloride ratio of 0.9 to 1.3, and, as a separate material from the antiperspirant salt, a stabilizing basic material suspended in the carrier in an amount sufficient to prevent degradation of said antiperspirant composition or to minimize acid odor.

2. The antiperspirant composition of claim 1 comprising, by weight, about 6% to 22% (USP) antiperspirant salt and about 0.1% to 10% stabilizing basic material.

3. The antiperspirant composition of claim 2 wherein the stabilizing basic material comprises a salt formed by a strong base and a weak acid, an amino acid that is basic (pH>7), a salt formed by a strong base and an amino acid, an inorganic base that is not soluble in water, or a mixture of two or more of these.

4. The antiperspirant composition of claim 3 wherein the stabilizing basic material comprises about 0.5% to 3% by weight of the composition.

5. The antiperspirant composition of claim 2 wherein the stabilizing basic material comprises an amino acid that has a pH>8 in aqueous solution.

6. The antiperspirant composition of claim 2 wherein the stabilizing basic material comprises glycine, lysine, tyrosine or arginine.

7. The antiperspirant composition of claim 2 wherein the stabilizing basic material comprises a salt formed by a strong base and an amino acid.

8. The antiperspirant composition of claim 2 wherein the stabilizing basic material comprises sodium glycinate, sodium tyrosinate, calcium glycinate, sodium lysinate, magnesium glycinate or strontium glycinate.

9. The antiperspirant composition of claim 2 wherein the stabilizing basic material comprises a salt formed by a strong base and a weak acid.

10. The antiperspirant composition of claim 2 wherein the stabilizing basic material comprises sodium carbonate, sodium bicarbonate, sodium acetate, potassium carbonate, potassium bicarbonate, sodium gluconate, sodium benzoate, sodium citrate, sodium phosphate, sodium hydrogenphosphate, sodium dihydrogenphosphate, sodium lactate, sodium tetraborate, or (di-, tri- or tetra-) sodium EDTA.

11. The antiperspirant composition of claim 2 wherein the stabilizing basic material comprises an inorganic base that is not soluble in water.

12. The antiperspirant composition of claim 2 wherein the stabilizing basic material comprises magnesium oxide, calcium oxide, strontium oxide, or zinc oxide.

13. The antiperspirant composition of claim 2 wherein the stabilizing basic material comprises sodium glycinate, lysine, or sodium carbonate.

14. The antiperspirant composition of claim 3, 6, 8, 10, 12 or 13 wherein the antiperspirant Bait comprises an aluminum-zirconium chlorohydrate having a metal to chloride ratio of 0.9 to 1.1.

15. The antiperspirant composition of claim 3 wherein the antiperspirant salt comprises an aluminum-zirconium chlorohydrate having a metal to chloride ratio of 0.9 to 1.0.

16. The antiperspirant composition of claim 3 wherein the carrier comprises a volatile silicone.

17. The antiperspirant composition of claim 3 in the form of a cream, gel, soft-solid, or solid stick.

18. The antiperspirant composition of claim 3 in the form of a solid stick, wherein the hardness of the stick is degraded by 20% or less when the stick is aged for one month at 45° C.

19. A method of reducing perspiration from human skin comprising applying to human skin a topical antiperspirant composition according to claim 3, 6, 8, 10, 12, 13 or 18.

* * * * *